United States Patent [19]
Jaeger

[11] Patent Number: 5,802,940
[45] Date of Patent: Sep. 8, 1998

[54] DISPENSER APPARATUS FOR AN ECONOMIC USE OF A MULTI-ZONE DISPOSABLE STRIP

[75] Inventor: Gérard Jaeger, Blonay, Switzerland

[73] Assignee: Asulab S.A., Bienne, Switzerland

[21] Appl. No.: 638,799

[22] Filed: Apr. 29, 1996

[30] Foreign Application Priority Data

May 2, 1995 [FR] France .................................. 95 05222

[51] Int. Cl.⁶ .................................................. B26D 5/20
[52] U.S. Cl. ........................... 83/207; 83/222; 83/229;
    83/257; 83/276; 206/531; 206/538; 221/74;
    225/16
[58] Field of Search ............................ 83/207, 222, 226,
    83/229, 257, 276; 225/10, 16; 221/70, 71,
    72, 73, 74; 206/530, 531, 538

[56] References Cited

U.S. PATENT DOCUMENTS

| | | | |
|---|---|---|---|
| 1,973,798 | 9/1934 | Crowley | 83/226 |
| 2,356,179 | 8/1944 | Proudman et al. | 83/257 |
| 3,395,829 | 8/1968 | Cogdell et al. | 221/70 X |
| 3,410,450 | 11/1968 | Fortenberry | 221/71 X |
| 3,454,194 | 7/1969 | Becker | 221/71 |
| 3,730,409 | 5/1973 | Ratti | 225/10 |
| 3,732,544 | 5/1973 | Obland | 364/479.06 |
| 3,903,773 | 9/1975 | Furukawa | 83/371 X |
| 4,240,202 | 12/1980 | Gilbert | 30/162 |
| 4,272,550 | 6/1981 | Feldstein | 221/71 |
| 4,733,797 | 3/1988 | Haber | 221/74 X |
| 4,770,322 | 9/1988 | Slota et al. | 225/16 X |
| 4,826,558 | 5/1989 | Wada et al. | 221/73 X |
| 5,014,429 | 5/1991 | McNamara | 30/162 |
| 5,502,396 | 3/1996 | Desarzens et al. | 324/713 |
| 5,525,297 | 6/1996 | Dinger et al. | 422/63 |

FOREIGN PATENT DOCUMENTS

| | | |
|---|---|---|
| 416507 | 3/1991 | European Pat. Off. . |
| 2710411 | 3/1995 | France . |
| 2710412 | 3/1995 | France . |
| 2710414 | 3/1995 | France . |

*Primary Examiner*—Maurina T. Rachuba
*Attorney, Agent, or Firm*—Sughrue, Mion, Zinn, Macpeak & Seas, PLLC

[57] ABSTRACT

A dispenser apparatus having a guiding plate (59) and a cylindrical extension (74) with a groove (75), the cylindrical extension preferably being coupled to a cover (22) for enabling backwards movement of a disposable strip (34) in the apparatus prior to the separation of a disposable zone (Z1 to Z9) of the strip. The strip can be moved forward step-by-step, after it has been inserted into the apparatus, via a sliding button (23) which acts on a cursor (35) to which the strip (34) can be coupled and which can circulate into a passage (29) provided in the case (20) of the apparatus. The apparatus is particularly applicable to dispensing devices for objects such as medical tablets, and to blood sugar level measuring devices.

11 Claims, 11 Drawing Sheets

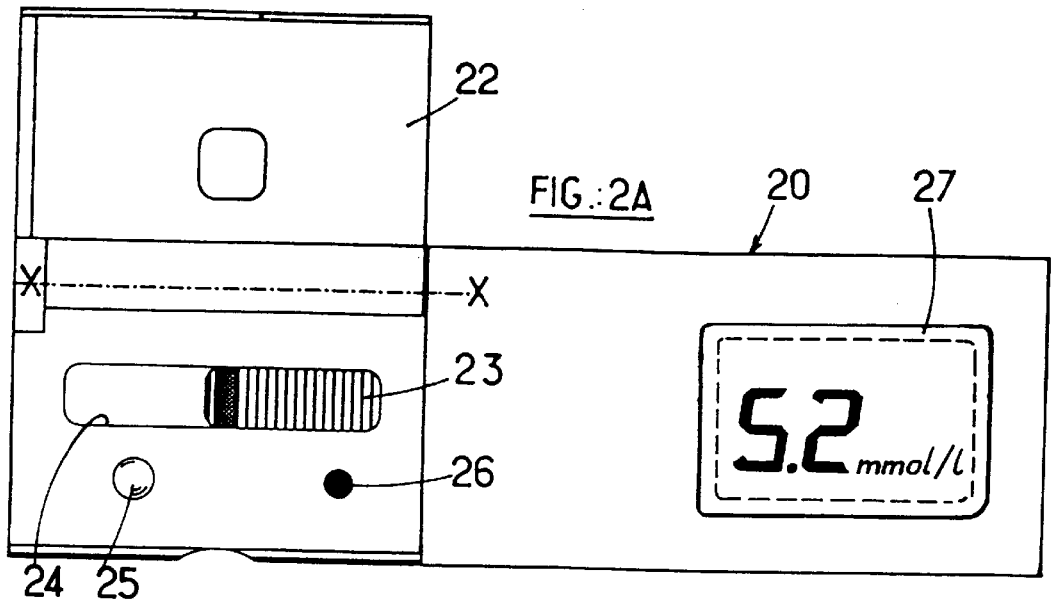
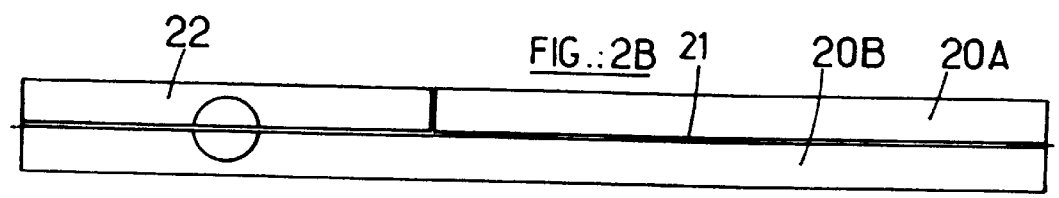
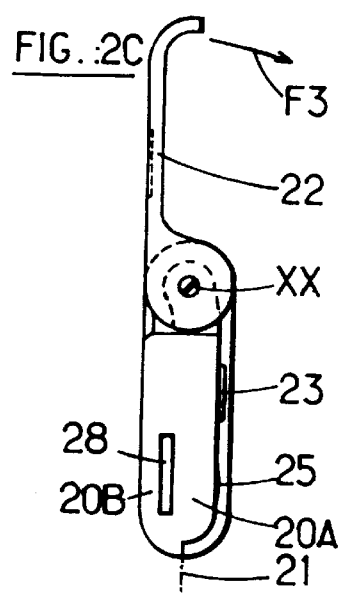

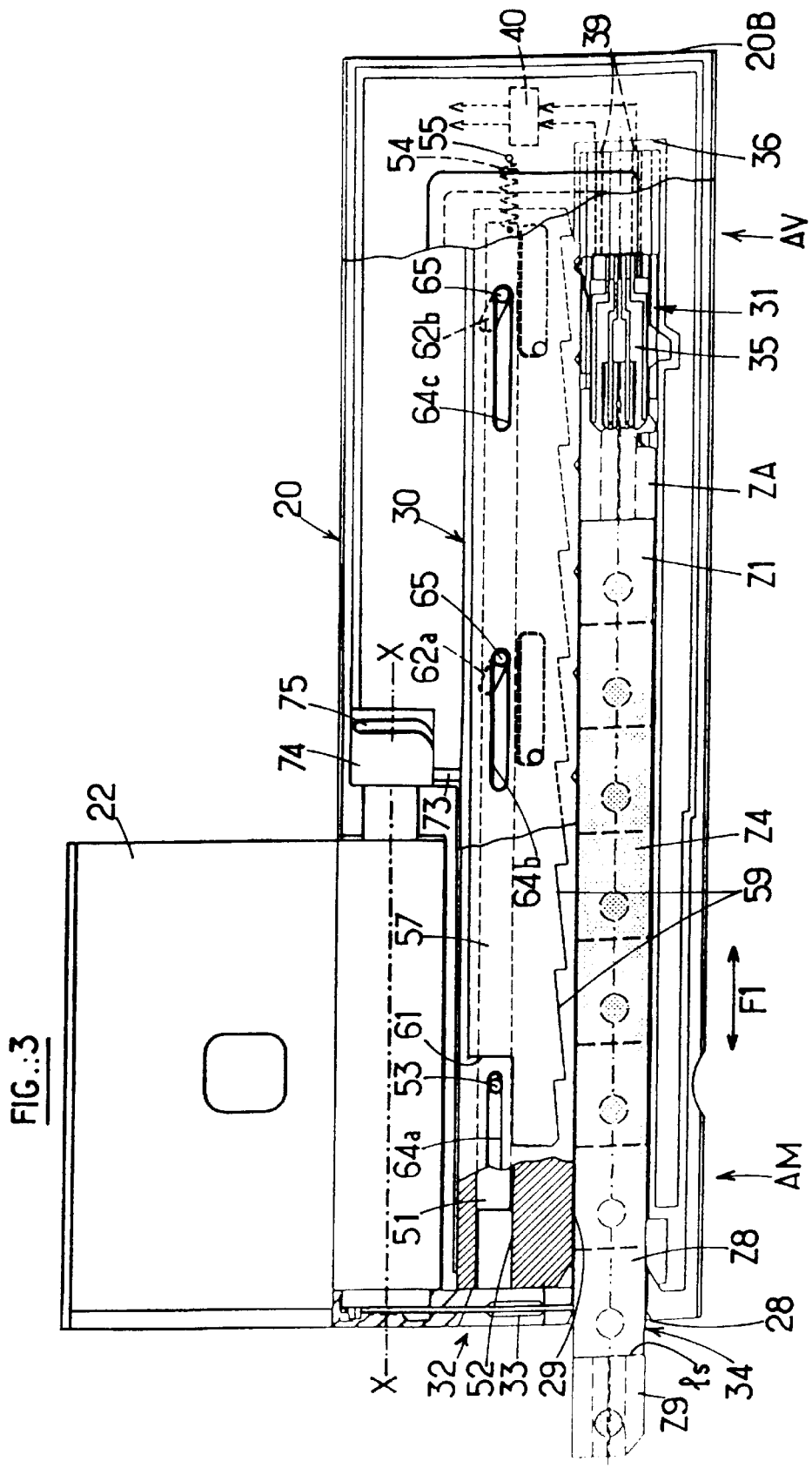

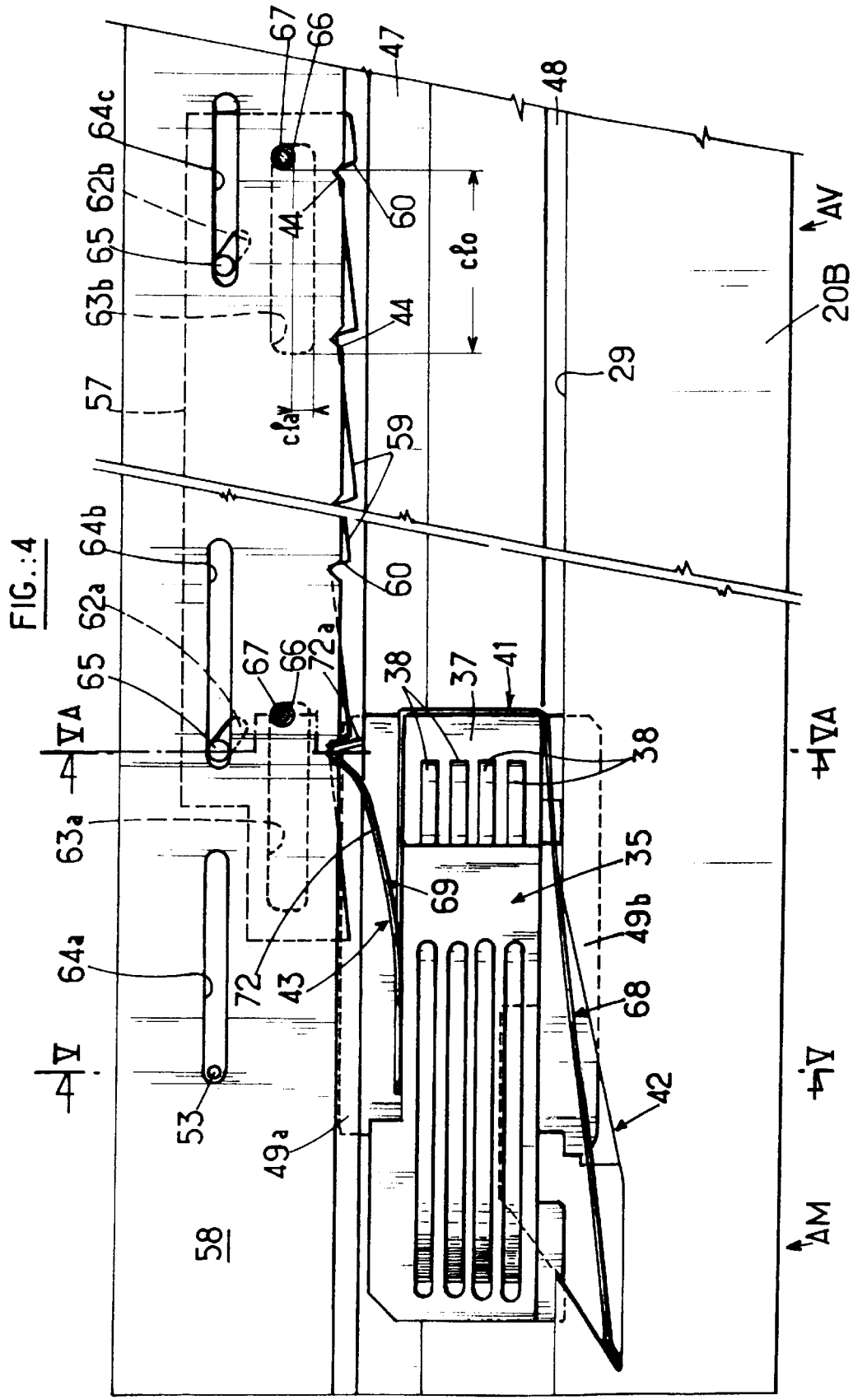

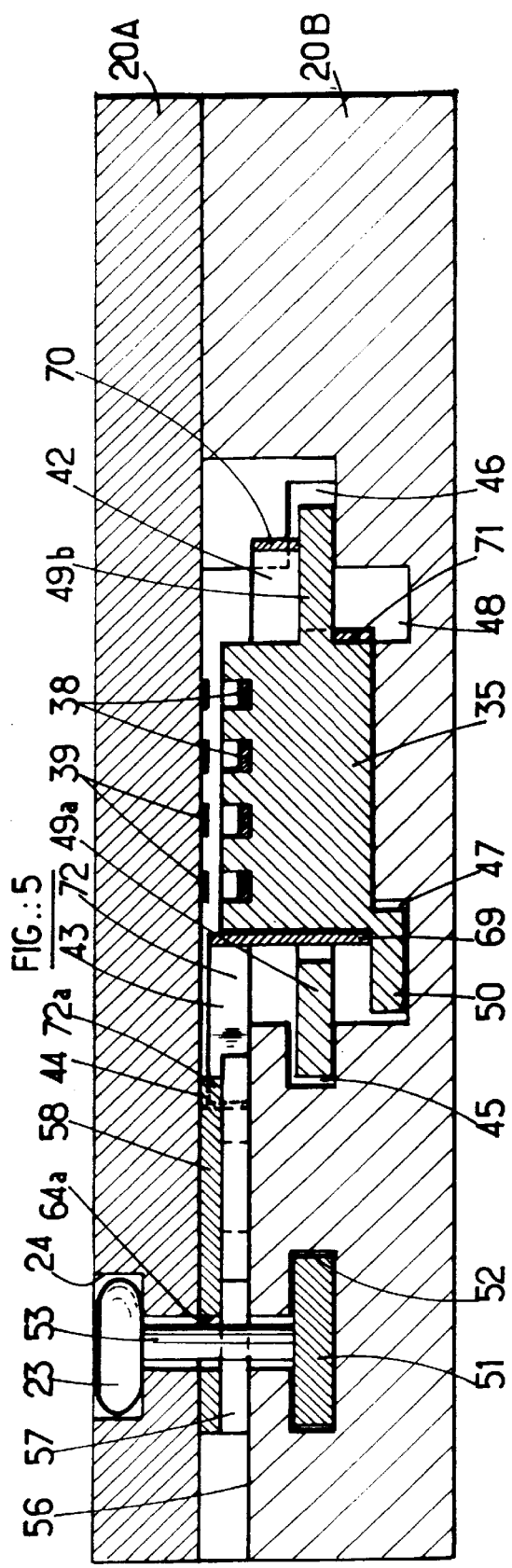

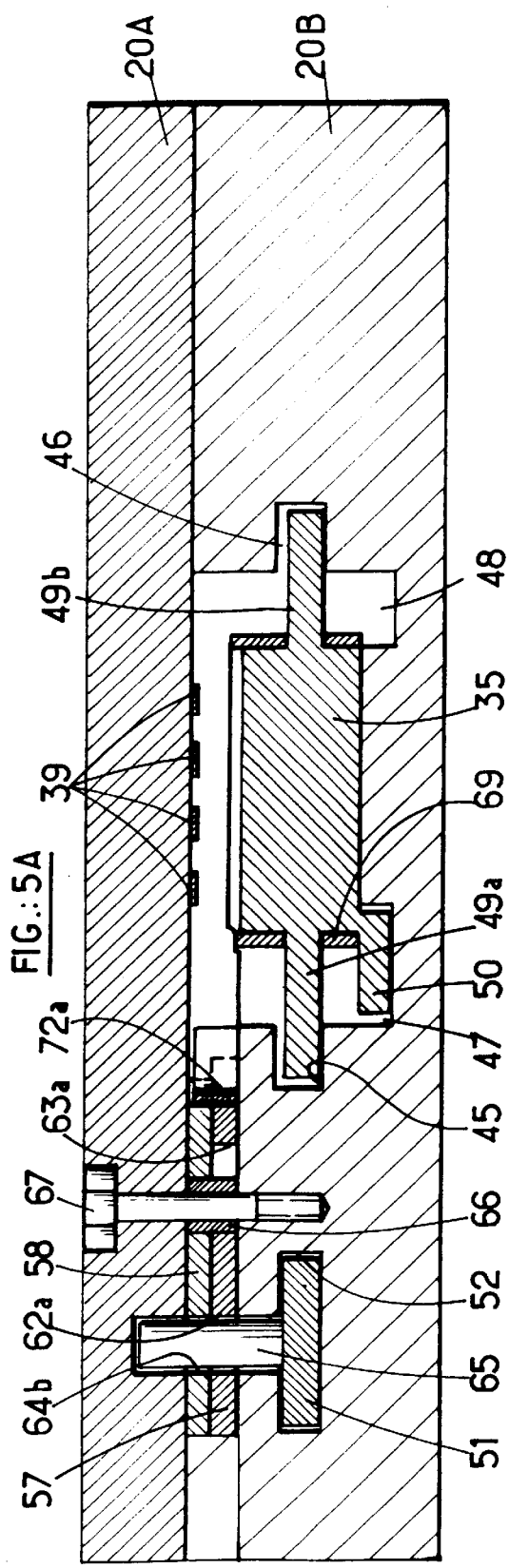

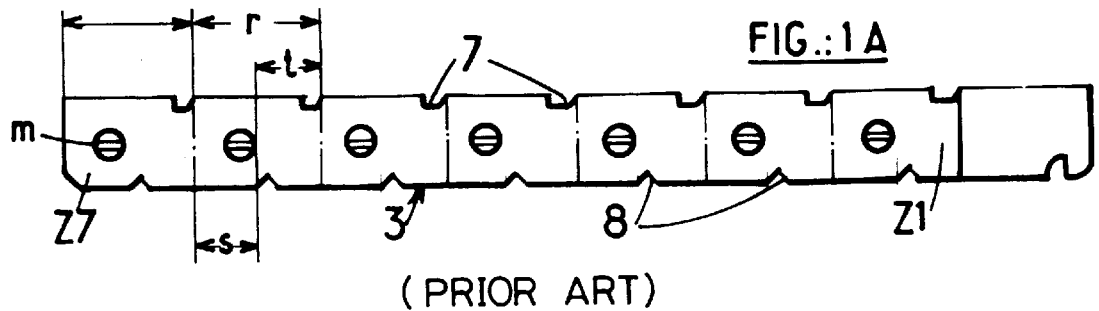
FIG.:1A
(PRIOR ART)
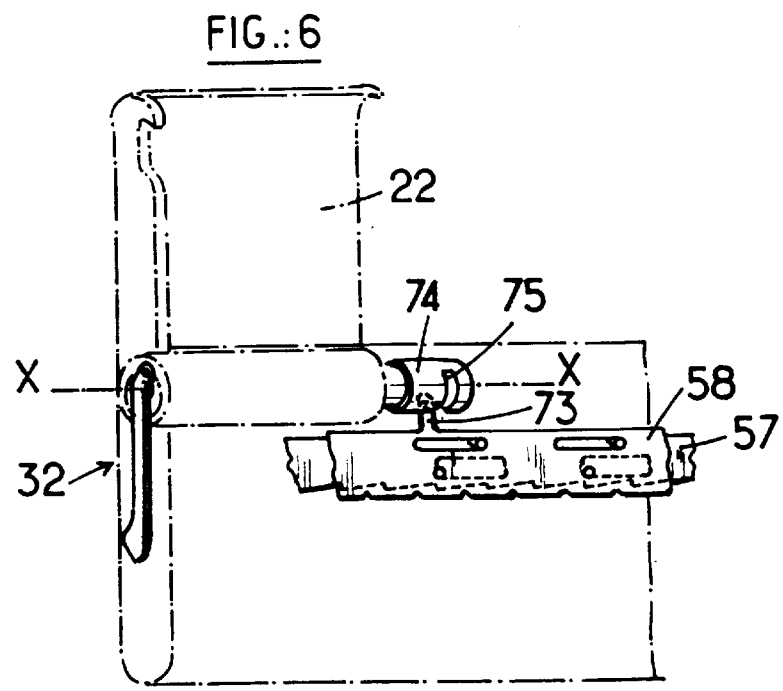
FIG.:6
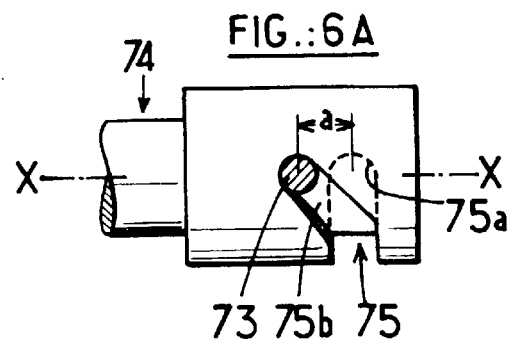
FIG.:6A

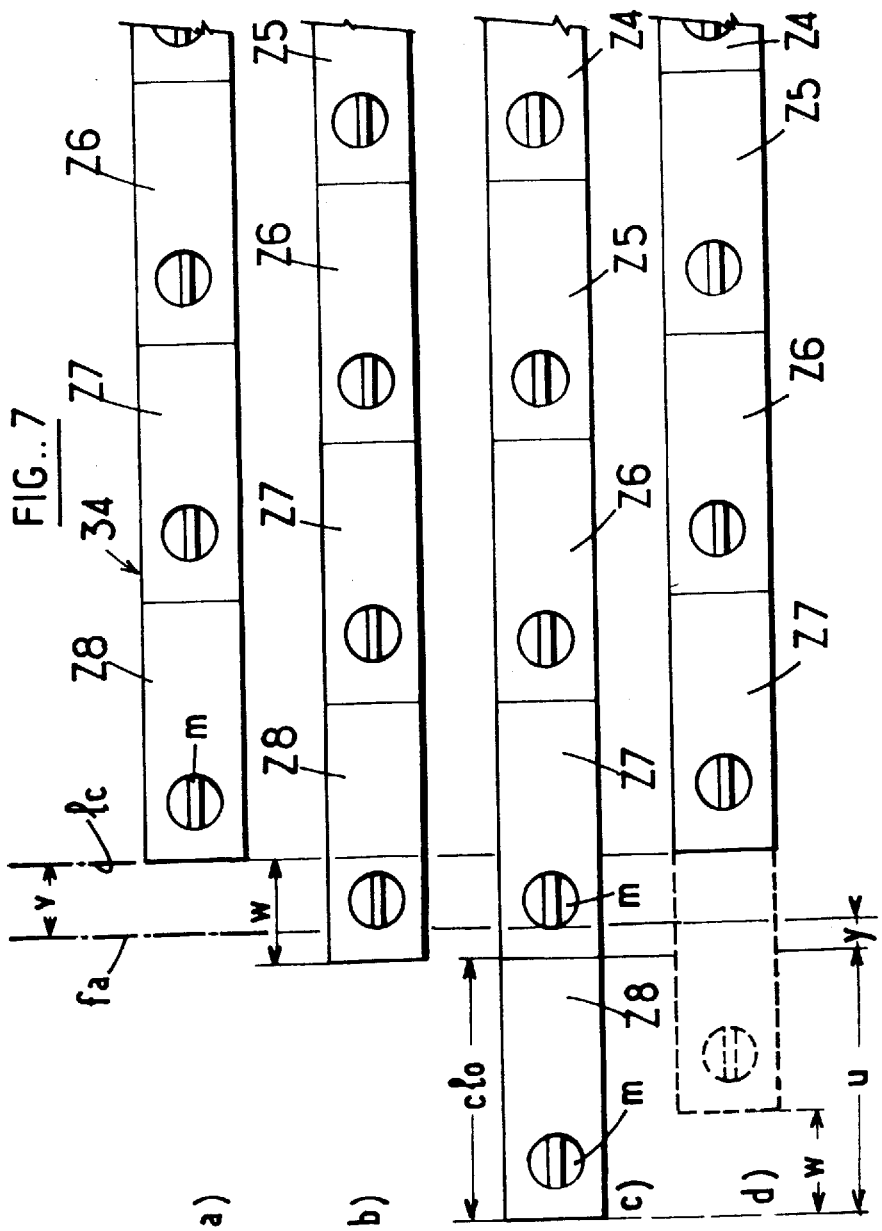

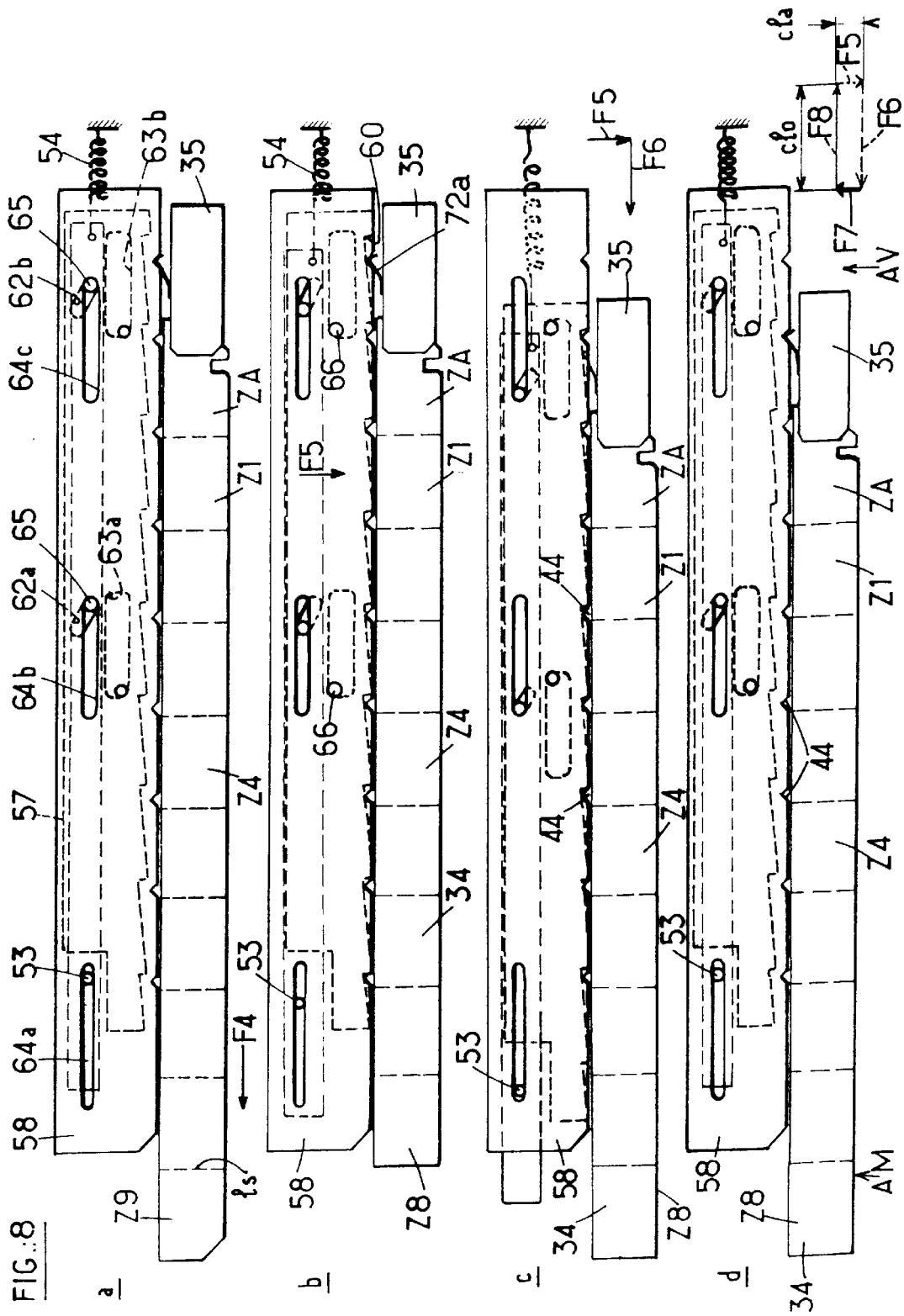

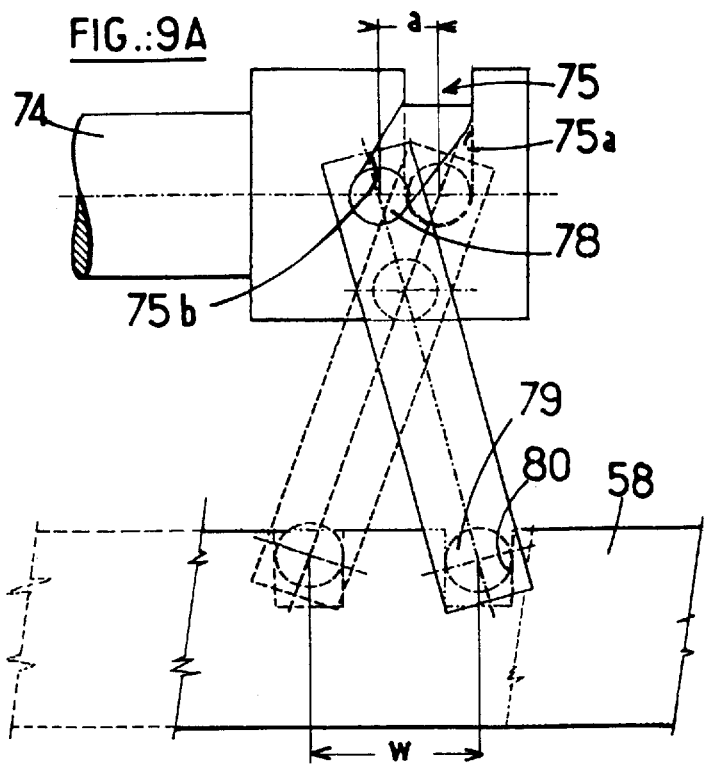
FIG.:9A
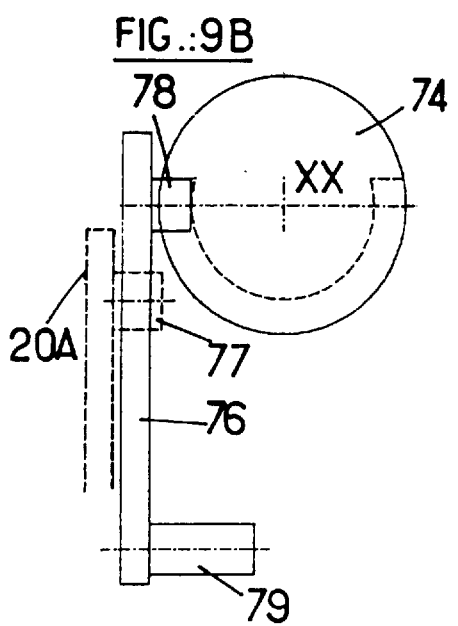
FIG.:9B

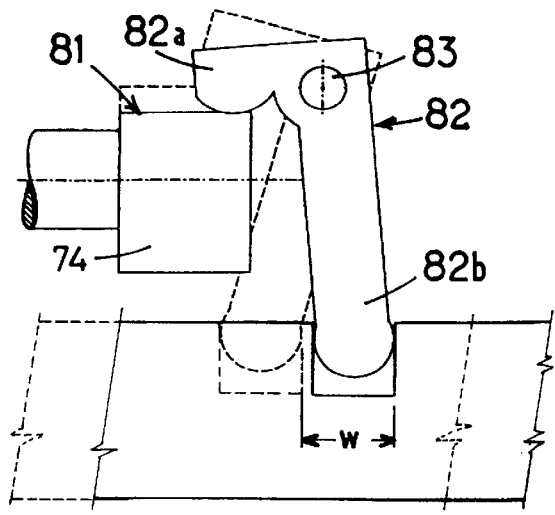
FIG.: 10A
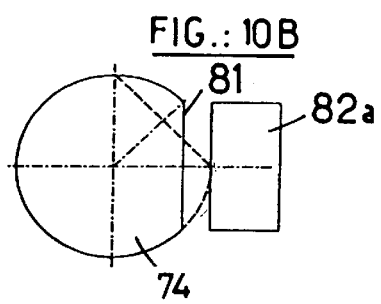
FIG.: 10B
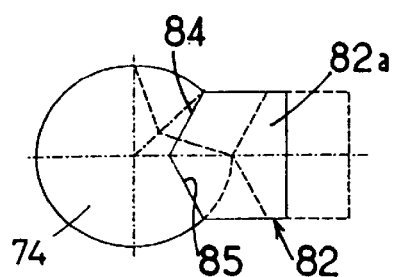
FIG.: 11

DISPENSER APPARATUS FOR AN ECONOMIC USE OF A MULTI-ZONE DISPOSABLE STRIP

BACKGROUND OF THE INVENTION

The present invention relates to a dispenser apparatus requiring the use of disposable elements in the shape of a strip to operate, each of these strips comprising in the longitudinal direction several successive utilisation zones intended to be detached from the strip after their use.

More particularly, the invention concerns an apparatus of this type forming a measuring device enabling a parameter of a substance deposited on successive zones of a strip forming a disposable measuring sensor, also called a multizone sensor, to be measured.

A measuring device of this type may advantageously be used for measuring blood sugar levels, for use by diabetics. Different aspects of such a device have been disclosed in several French patents filed in the name of the applicant and amongst which one may cite U.S. Pat. No 5,395,504 as regards the electrochemical measuring method used, and U.S. Pat. No 5,525,297 as regards a cutting device enabling the used measuring zones to be detached from the disposable strip.

FIG. 1 of the attached drawings shows a measuring device in which one finds, in summary form, an embodiment example of the improvements which were the subject of the aforementioned U.S. patents, it being understood that in order to find a detailed description of them, one may refer to the texts of said patents.

Thus, the measuring device comprises a case 1, of a general elongated shape and of such a size that it can easily be held in the palm of an adult's hand. This case defines a circulation passage 2 longitudinally oriented in case 1 and intended for the circulation of a sensor strip 3 (double arrow F1) and a cursor 4. The latter is responsible for transmitting the electric signal coming from sensor strip 3 to electric lines 5 which extend along passage 2. These lines are in turn connected to an electronic circuit 6 intended to process this electric signal in a suitable manner to make it intelligible to a user by means of a display device which is also provided in case 1.

In the example of FIG. 1, sensor strip 3 is specifically adapted for measuring blood sugar levels. A detailed description of a strip of this type can be found in the first patent cited above. One need only keep in mind here that it comprises several measuring zones, seven in this case referenced Z1 to Z7 of which the first zone Z7 shown in dotted lines is assumed already to have been used and detached from strip 3.

It will also be noted that the sensor strip comprises for each of zones Z1 to Z7 a forward feed catch 7 (FIG. 1A) on one of its longitudinal edges and, for all of the zones, a positioning notch 8 situated on the other edge of the strip.

Forward feed catches 7 co-operate with a longitudinal forward feed mechanism 9 of strip 3 along its passage 2. Forward feed mechanism 9 comprises a control button (not visible in FIG. 1) mounted so as to slide longitudinally in the case, that is to say, as seen in FIG. 1, above passage 2.

The control button co-operates with a rotating latch 10 guided on two studs 11 and 12 which are attached to a bar 13. The latter is coupled to the control button and mounted so as to slide in case 1 in the direction of arrow F1 against the action of a return spring 14 fixed to case 1. Rotating latch 10 is held in a non active position (shown in FIG. 1) by a leaf spring 15 and comprises an actuating nose 16 intended to co-operate with forward feed catches 7 of sensor strip 3.

Thus, it is understood that when the control button is activated back and forth, the sensor strip moves forward the length of a measuring zone of the strip, the forward feed mechanism causing latch 10 to rotate in a reciprocating manner (along arrow F2) to first of all push the strip out of the passage by one step and then to return to the inactive position as shown by disengaging itself from the strip.

The device also comprises a cover 17 rotatably mounted on the case about an axis X—X and mechanically coupled to a cutting mechanism 18 enabling the disposable zone of the strip which has just been used to be cut, by a simple closing movement of cover 17.

It is also to be noted that cursor 4 slides freely in passage 2 and is mechanically coupled to disposable sensor strip 3 during its insertion in the apparatus, when cursor 4 abuts the bottom of passage 2. The cursor carries for this purpose a resilient coupling member which yields to the insertion force exerted on strip 3 by the user, in order to latch onto this strip as soon as the insertion force is released.

FIG. 1A of the attached drawings shows a sensor strip 3 of the prior art before it has been inserted into the apparatus.

Each zone has a length r selected so that when the zone is taken out of the apparatus to be used, the user has sufficient space available to perform the action which he has to carry out on this zone. In the specific application described here, this action is the depositing of a drop of blood in the area m where the sugar level measurement has to be carried out. Length r must be equal to the forward feed pitch of the strip, when it is moved to present the following measuring zone.

It will be noted, however, that area m in which the measurement is actually carried out far from occupies the entire surface of the zone and that for ease of operation, this area is preferably situated as close as possible to the end of the opposite zone to that through which it is introduced into passage 2.

In other words, this area only occupies a length s of the strip, the empty area in each zone of the strip having a length t whose only use is to respect the distance at which the zone has to come out of the apparatus during its use (r=s+t). Consequently, the strip must have a total length markedly greater than the total length strictly necessary for the seven measuring areas m of the strip.

This requirement has a direct consequence on the length which passage 2 must have and consequently on the total length of the apparatus. It is clear that for the user an apparatus with the smallest dimensions possible is an advantage, in particular in the context of the application described here, since in this case, the apparatus is usually in the user's pocket or handbag.

OBJECT OF THE INVENTION

An aim of the invention is thus to provide a dispensing apparatus which uses disposable strips of small length for a given number of measuring zones, and which consequently also has a small length.

SUMMARY OF THE INVENTION

The invention thus concerns a dispensing apparatus requiring the use of disposable elements having the shape of strips to operate, each of these strips comprising in the longitudinal direction several successive utilisation zones intended to be detached from the strip after their use, said apparatus comprising:

a case with an hinged cover, said case defining a circulation passage for said strips, said passage having, taking account of the direction in which said strips are introduced, an upstream end and a downstream end, a forward feed mechanism for bringing said strip out of the circulation passage in accordance with a step by step movement after its introduction into the latter by a user, and a sliding unit mounted so as to move in said passage, operationally coupled to said forward feed mechanism and intended to be coupled to the downstream end of said strip when it is introduced by the user, said dispenser apparatus being characterized in that it also comprises a guiding plate, a cylindrical extension of the cover provided with a groove, the whole forming control means for enabling the backward movement of said strip over a predetermined distance, which is shorter than a forward step of this strip, after it has carried out such a step.

As a result of these features, each zone of the strip may occupy a comparatively shorter length than in the past. Indeed, while a zone n of the strip is used, the latter may be out of the apparatus by a length greater than the length of the zone concerned, while zone n+1 is also out, by at least a certain part of its length. After the use of zone n, zone n+1 may then be brought back inside the apparatus by the backwards movement means, which protects it from any deterioration.

In these circumstances, it becomes possible to provide more zones on the strip than was possible in the past. In a practical example, where the strip comprises nine zones, one can thus shorten it by for example 50 mm or alternatively for a same strip length, to provide more zones. If one chooses the first solution, a shorter strip enables the size of the apparatus to be reduced, thus making it easier to use.

BRIEF DESCRIPTION OF THE DRAWINGS

Other features and advantages of the invention will appear during the following description, which is given solely by way of example and made with reference to the attached drawings in which:

FIG. 1A is a plan view showing a disposable strip according to the prior art, intended to be used in the dispensing apparatus of FIG. 1;

FIGS. 2A, 2B and 2C are three exterior views, according to three orthogonal planes, of a dispensing apparatus according to the invention;

FIG. 3 is a plane view of a dispensing apparatus according to the invention, the upper part of its case being assumed to have been removed and certain parts of it being shown partially cut away;

FIG. 4 is a larger scale plane view, of the apparatus according to the invention, and in particular, of the construction of the forward feed mechanism;

FIGS. 5 and 5A are cross-sectional views taken respectively along lines V—V and VA—VA of FIG. 4;

FIGS. 6 and 6A are respectively perspective and exterior partial views of the apparatus, showing more particularly the cover and the cutting mechanism;

FIG. 7 illustrates more particularly the advantages which the invention enables to be obtained;

FIGS. 8a, 8b, 8c, and 8d show in four views, the kinematics of the disposable strip displacement means used in the apparatus according to the invention;

FIGS. 9A and 9B show via respective orthogonal views an alternative embodiment of the invention;

FIGS. 10A and 10B shown similar views of another alternative embodiment, and

FIG. 11 shows a third alternative embodiment of the invention.

DETAILED DESCRIPTION OF PREFERRED EMBODIMENTS OF THE INVENTION

Figure 1:
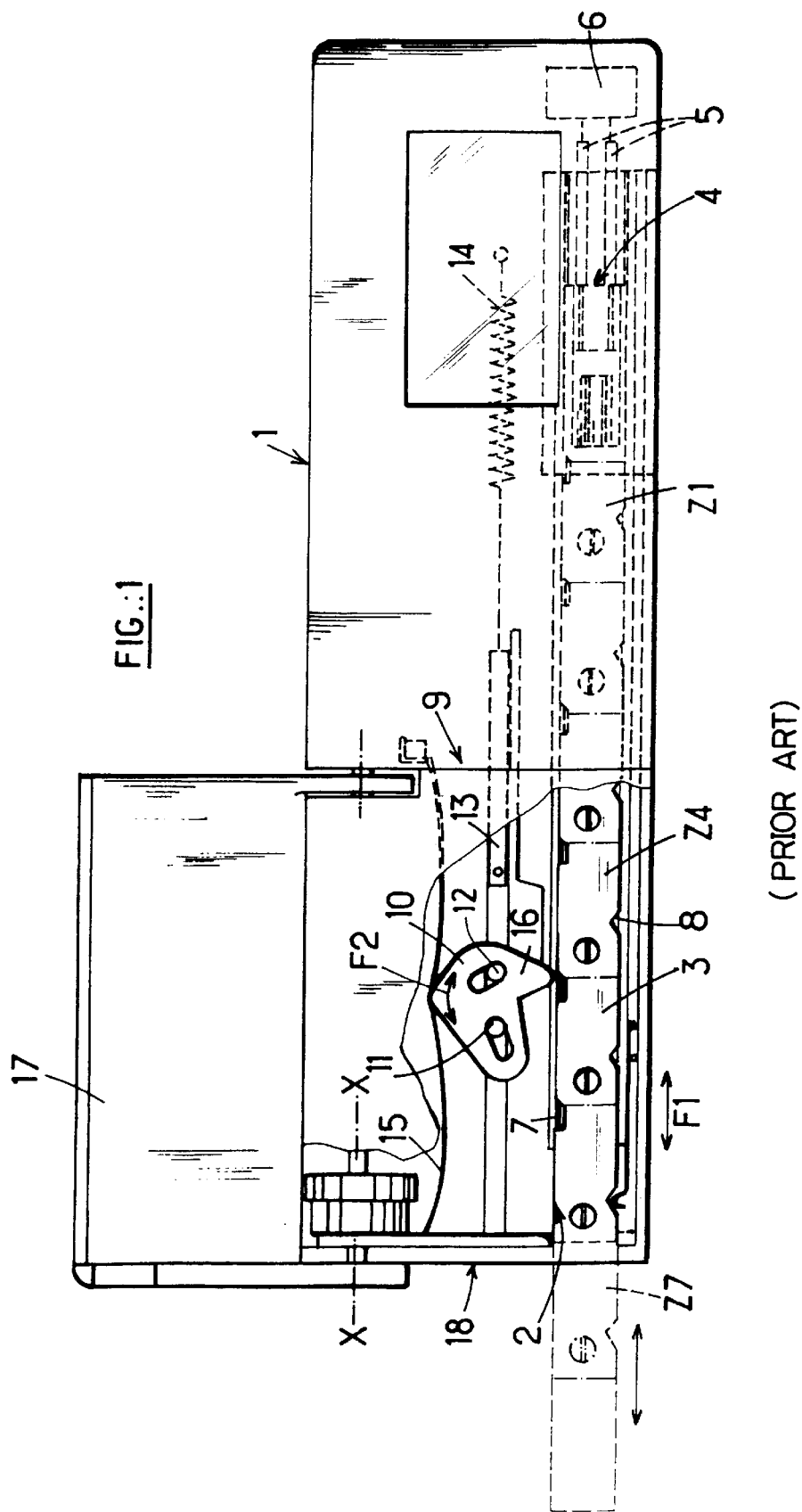
FIG. 1, already described, is a schematical plan view, partially cut away, of a dispensing apparatus according to the aforecited patent applications.

FIGS. 2 to 5 show a preferred embodiment of the dispenser apparatus according to the invention in its application to a device enabling blood sugar levels to be measured for use by diabetics, for example. However, the invention is not limited to this specific application. Indeed, it may be implemented in all sorts of other applications in which it is desirable to use disposable strips on which adjacent zones define a specific utilisation area, these zones after having been used being able, or even having to be (for medical reasons for example) removed from the strip to make room for a following zone. For example, in the medical field, an apparatus of this type could be used for dispensing a series of medical tablets or pills required, in accordance with the dosage prescribed by the doctor, to be taken in a strict order defined in advance. However, the invention is not limited either to applications in the medical field.

The dispenser apparatus according to the invention shown in FIGS. 2 to 6 comprises a case 20 made of two half shells 20A and 20B, preferably in a moulded plastic material, and assembled along a parting line 21. In the application described, case 20 has an elongated shape and dimensions such that it can easily be held in the palm of an adult's hand.

The apparatus comprises a cover 22 extending over part of its length which is hinged onto case 20 about a longitudinal axis X—X.

In FIGS. 2A and 2C, cover 22 has been shown in an open position and it can be closed by making it rotate in the direction of arrow F3. When it is open one can see a button 23 which slides in a guide 24 arranged in upper half shell 20A of case 20. A small magnifying lens 25 enables a portion of the disposable strip (not shown here) which is slid inside the apparatus to be observed. A push button 26 is intended to recall previously taken measurements stored in the memory of the apparatus, for display on a display 27 also used to enable the results of the measurement which has just been made to be read immediately.

It is to be noted that the apparatus is switched on as soon as button 23 is activated and its power supply (preferably an incorporated battery) is switched off after the lapse of a predetermined period of time (60 seconds for example) defined from the moment when any manipulation of the apparatus by the user has ceased.

From the side of cover 22, on the front lateral narrow edge of case 20, the apparatus has an opening 28 which is the mouth of a circulation passage 29 (FIG. 3) of the disposable strips.

FIG. 3 shows the dispensing apparatus according to the invention with upper half shell 20A having been removed. Consequently, several operating units can be observed, and in particular:

a forward feed mechanism 30 which enables a disposable strip to be fed step by step into passage 29 via the repeated action of sliding button 23 and also its backwards movement to be assured;

a sliding unit 31, which is intended to be coupled to a disposable strip and which slides into passage 29;

a cutting unit 32 situated along the end narrow edge of the apparatus and comprising a blade 33 mounted so as to slide in a perpendicular direction to axis X—X; and a disposable strip 34 having measuring zones Z1, Z2 . . . etc. and a zone ZA forming a leader zone of the strip and enabling it to be coupled to sliding unit 31.

Sliding unit 31 comprises a cursor 35 capable of circulating in passage 29 which is blocked at its end 36 opposite opening 28. This end will be referred to below as "downstream end" AV in view of the movement of introduction of strip 34 into passage 29. Of course, the opposite end, close to opening 28 will be called "upstream end" AM. These terms will also be used for the disposable strip, its downstream end thus being situated close to leader zone ZA.

Cursor 35 comprises a cursor body 37 (FIG. 4) carrying electric transmission means 38 for assuring the pick up of electric signals from strip 34 and the transmission of these signals to contact strips 39 which run along the upper wall of passage 29. Contact strips 39 are connected to an electronic processing circuit 40 (FIG. 3) which is in turn connected to display 27. According to an alternative embodiment a flexible cable for the transmission of the signals could also be provided, this cable gradually extending into passage 29 as the cursor reaches upstream end AM of the passage.

Body 37 also carries resilient blocking and coupling means 41 which co-operate with cam and stop forming means 42 which are in one piece with lower half shell 20B of case 20.

Body 37 further comprises driving and positioning means 43 intended to co-operate with forward feed mechanism 30 and with indexing catches 44 which are provided along passage 29 and respectively define the measuring positions of strip 34.

In FIGS. 4, 5 and 5A in particular, one sees that guiding passage 29 has two lateral longitudinal grooves 45, 46 and two longitudinal grooves 47 and 48 arranged in its bottom. Body 37 is of a general parallelepipedal shape from which two lateral ribs 49a and 49b protrude, respectively fitting into lateral grooves 45 and 46 and a lower rib 50 which fits into groove 47 provided in the bottom of passage 29.

Forward feed mechanism 30 comprise a bar 51 of rectangular section mounted freely in a longitudinal groove 52 of reverse T-shaped section provided in half shell 20B. This bar 51 is attached to a first rod 53 protruding from groove 52 and passing through half shell 20A to be driven into sliding button 23.

Bar 51 is permanently drawn in direction AV via a return spring 54, housed at the upstream end of groove 52 (FIG. 3). This return spring 54 is fixed to bar 51 via one end, while its opposite end is fixed onto a small spigot 55 in one piece with half shell 20B and situated at the downstream end of groove 52.

A part of the upper surface of half shell 20B forms a sliding surface 56 extending along passage 29. It acts as support to a ratchet bar 57 intended to slide in a reciprocating manner along the direction of the double arrow F1.

This ratchet bar 57 is caught between sliding surface 56 and an elongated guiding plate 58 disposed above ratchet bar 57. The guiding plate 58 is also mounted so as to slide in the case of the apparatus in the direction of arrow F1 while indexing catches 44 for sliding unit 31 are provided in the edge of this guiding plate 58.

The edge of ratchet bar 57 running along passage 29 has a serrated edged toothing 59, the short flank 60 of each tooth being situated on downstream side AV.

The number of teeth of this toothing is equal to the number of zones provided on a disposable strip 34 having the maximum length acceptable to the apparatus. It is to be noted that the latter can accept disposable strips of any length between this maximum length and that corresponding to a minimum number of zones which it is reasonably useful to provide on the disposable strip (in theory, one could provide only one zone on the strip).

Ratchet bar 57 also has:

a front cut 61 (FIG. 3) extending in the lengthways direction of the bar, above the longitudinal groove 52 for enabling in particular the movement of rod 53 when button 23 is activated;

two cuts 62a and 62b having the shape of an oblong opening placed obliquely with respect to the general longitudinal direction of the bar, that is to say, to the direction of double arrow F1; and two rectangular shaped slots 63a and 63b used to limit the longitudinal travel clo and the lateral travel cla of ratchet bar 57.

Guiding plate 58 has three elongated slots 64a, 64b and 64c, aligned on top of each other in the longitudinal direction, thus in the direction of double arrow F1.

Rod 53 which has already been mentioned, passes through the first of these slots 64a. Driving rods 65 pass through the second 64b and third 64c slots and also through oblong openings 62a and 62b of ratchet bar 57. The driving rods 65 are fixed onto bar 51 and thus move simultaneously with button 23.

Sleeves 66, which act as distance sleeves and through which tightening screws 67 screwed into half shell 20B also pass, pass through cuts 63a and 63b. These sleeves allow bar 57 and plate 58 to move along their own plane without too much friction.

As already mentioned above, the length of cuts 63a and 63b define the longitudinal travel clo of the ratchet bar, while their width determines its lateral travel cla (FIG. 4). In this way, cuts 63a and 63b in co-operation with sleeves 66 assure the definition of the movement of bar 57 along an orbital path having a rectangular outline.

Resilient blocking and coupling means 41 and driving and positioning means 43, designed for securing a strip 34 to the cursor 35, are preferably made in a same spring plate. The latter is U-shaped and may for example be compound filled with the plastic material when cursor 35 is moulded. The central branch of the U is applied against the downstream face of cursor 35 while its lateral branches 68 and 69 extend towards opening 28 of passage 29 running respectively along the lateral sides of cursor 35.

Branch 68 comprises two springs 70 and 71 intended to assure the blocking of cursor 35 in upstream position AM and to release it as soon as a disposable strip is inserted in passage 29. Since this aspect of the apparatus does not form part of the invention, it will not be described in more detail here.

Branch 69 constitutes in fact driving and positioning means 43 which have already been mentioned. It comprises a spring 72 extending downstream and ending in a hook 72a. The latter is intended to co-operate with catches 44 and also with toothing 59 of ratchet bar 57.

It will be noted that the edges of the disposable strip do not comprise any notches or other elements necessary to drive the strip. Indeed, this driving is assured exclusively via cursor 35 on which forward feed mechanism 30 acts. The shape of the disposable strip is thus very simple.

FIG. 6 in particular shows that, according to a particular feature of the invention, guiding plate 58 comprises a lateral finger 73 which extends from one of its lateral edges in the direction of the hinge axis X—X of cover 22.

On the side opposite cutting unit 32, the cover 22 comprises a cylindrical extension 74 whose cylindrical surface, also having an axis X—X, comprises a groove 75, a first portion 75a of which is outlined in a radial plane in relation to axis X—X and a second portion 75b of which has a helical outline having an axis X—X. Finger 73 has a length such that its end penetrates groove 75 which thus acts as a cam for it.

The guiding means 58, the cylindrical extension 74 and its groove 75 are as a whole the control means for enabling the movement of the disposable strip 34.

The groove is placed angularly so that, when cover 22 is closed, finger 73 is situated at the end of straight portion 75a far from helical portion 75b.

Conversely, when cover 22 is in an open position, finger 73 is situated at the end of helical portion 75b opposite straight portion 75a.

As a result, during the opening movement of cover 22, finger 73, and consequently guiding plate 58, are moved from downstream side AV towards upstream side AM and conversely, during the closing movement, plate 58 moves in the opposite direction, that is to say that it moves backwards considering the direction in which disposable strip 34 moves out.

The two movements cause a displacement, in one direction or the other, of catches 44 along passage 29, which results in fact in a movement of cursor 35 in the corresponding direction along passage 29. Spring 72 remains engaged, via its hook 72a, with one of these catches 44, until button 23 is actuated.

It is to be noted however that to co-ordinate the longitudinal movement of cursor 35 with the cutting operation carried out by cutting unit 32, the movements only occur during a part of the rotation movement of cover 22, namely while finger 73 is situated in helical portion 75b of groove 75. This is why the angular positioning of this helical portion 75b of groove 75 must be carefully chosen.

The amplitude of the longitudinal movement is chosen in particular as a function of the desirable distance at which a given zone of the disposable strip must move out of the apparatus for the user to be able comfortably to carry out the corresponding operation. For example, within the framework of the specific example of the sugar level measurement, the user must easily be able to deposit a drop of blood on measuring area m of each zone.

Referring to FIG. 7, it is admitted that this distance is equal to u for example, measured from the upstream face fa of case 20. This face fa is situated at certain distance v from cutting line 1c of the blade of cutting unit 32, taking into account in particular the thickness of the wall of case 20 at this place.

In FIG. 7, the position of disposable strip 34 when zone Z9 has just been cut from it is shown at a). The upstream edge of this zone (still considering the direction of introduction of strip 34) is then aligned along cutting line 1c. Cover 22 is still closed.

The user then opens the apparatus by flipping cover 22. This causes strip 34 to move forward by a distance w equal to the axial length of helical portion 75b of groove 75. This situation appears in b) in FIG. 7. One sees that distance w is slightly greater than distance v by a quantity y, for example.

During this opening operation of cover 22, finger 73 is moved thereby driving guiding plate 58 and, via the intermediary of corresponding catch 44 of the latter and of spring 72, cursor 35 and strip 34.

Next, button 23 is activated to move the disposable strip forward by one step the length of a zone (that is to say length clo, the operation in this respect being described in detail below). The strip is then in the position shown in FIG. 7 at c). The length of the strip which is out is thus equal to u=clo+y, that is to say sufficient to enable measuring area m to be used comfortably.

The user can then carry out the appropriate operation on the disposable strip, for example, depositing a drop of blood on measuring area m of zone Z8, removing a pill or other similar object attached to the strip in this zone, etc. This operation is facilitated by the fact that measuring area m of zone Z8 is situated relatively far from face fa of the case. It will be noted that, in the example shown, measuring area m of the following zone Z7 remains before front face fa of the case inside the latter. The measuring area of this zone Z7 thus cannot be deteriorated by an incorrect manipulation.

After completing the measuring operation, the user can then close the apparatus again, which first causes the strip to move backwards by distance w, then causes zone Z8 to be cut by cutting unit 32. Zone Z7 is then ready to be used (FIG. 7 at d)).

FIG. 7 clearly shows the advantage provided by the arrangement according to the invention. Indeed, without the forward movement and especially the backwards movement of the strip by distance w after the zone concerned is used, it would be necessary to move the strip forward by a step equal to w+clo. In other words, according to the nvention each zone of the strip can be shorter by w.

A practical example shows that this advantage is significant. Assuming that displacement w due to the movement of the cover is 7 mm, it is possible to gain 7 mm per zone. If one wishes to use strips having nine zones, for example, one can then gain 63 mm in strip length and reduce the corresponding dimension of the case by the same amount. Alternatively, for a same strip length, one can increase in a corresponding manner the number of zones of each strip.

It is to be noted that in the embodiment which has just been described, the strip necessarily undergoes a forward movement, then a backwards movement as a result of the rotation of cover 22. However, it is possible not only to disassociate the two movements from each other, but also to provoke them separately by other mechanical means than those described above. For example, the previous forward movement could be joined to that carried out with the aid of button 23. Furthermore, the backwards movement prior to the cutting, could be achieved using other mechanical means actuated in a different way.

The functioning of forward feed mechanism 30 will now be described in more detail.

In FIG. 3, the apparatus has been shown schematically when the user has just inserted a disposable strip into it. However, the strip has not yet entirely reached the end of passage 29. For this to happen, the (fictitious) line of separation ls between zones Z8 and Z9 must be placed before the cutting edge of cutting unit 32.

The forward feed mechanism is inoperative; ratchet bar 57 is thus in its downstream position, its toothing 59 being outside passage 29.

Conversely, in FIG. 4, cursor 35 is in the extreme upstream position in passage 29 with no strip being present in the apparatus. However, one assumes in this figure that the user has just manoeuvered button 23 for the last time, that leader zone ZA has already been ejected from the apparatus, but that the user has not yet released button 23. Consequently, in this configuration, ratchet bar 57 is still in its upstream position AM, return spring 54 is taut and short flank 60 of the most upstream tooth of toothing 59 is still engaged with hook 72a of spring 72. Furthermore, rod 53 engaged in button 23 is at the downstream end of slot 64a of guiding plate 58.

The four views a to d of FIG. 8 show the main positions of the components of the apparatus according to the invention during a complete forward feed cycle of the disposable strip provoked uniquely by movement of button 23. As has been seen previously, the forward or backwards travel due to the opening and closing movements of cover 22 are added to this cycle, said movements having been deliberately omitted from this drawing to avoid making it complicated to read. In the four representations of FIG. FIG. 8, it is thus assumed that the cover is held open.

More precisely, in FIG. 8a and as compared to FIG. 3, disposable strip 34 is completely inserted in the apparatus, cursor 35 being thus at the travel end at the downstream end of passage 29.

Return spring 54 holds ratchet bar 57 in the downstream position and due to the obliquity of slots 62a and 62b, this bar occupies the external lateral position in relation to passage 29.

Zone Z9 of the strip which then protrudes from the apparatus, may thus be used for a sugar level measurement. When the user has finished this measurement, he closes cover 22 which allows the process already described in connection with FIG. 7 to take place (backwards movement of the strip and cutting of zone Z7 along separation line ls with zone Z8).

The user must then make zone Z8 move out of the apparatus when using it again. In order to do this, he opens cover 22 (forward movement of the strip over a distance w, not represented in FIG. 8), then actuates button 23 in the direction of arrow F4 (FIG. 8b). The result of this is firstly the configuration of the components shown in this Figure, a configuration which is only transitory, but which shows that ratchet bar 57 moves first laterally inwards in the direction of arrow F5 over travel cla, again due to the obliquity of slots 62a and 62b. Toothing 59 is then placed in the active area of spring 72.

Since button 23 continues to be pushed forward, the most downstream short flank 60 of toothing 59 then comes into contact with hook 72a of spring 72, against the force of return spring 54 which is attached to bar 51, then this hook exerts a driving force on cursor 35. The latter thus moves towards upstream end AM of passage 29 pushing disposable strip 34 in front of it (in the direction of arrow F6).

The movement in this direction stops, when travel clo is completed, that is to say when the downstream edges of cuts 63a and 63b come into contact with sleeves 66 which are engaged around screws 67. Since this travel corresponds exactly to length clo of a zone on disposable strip 34, zone Z6 is thus outside the apparatus.

The user then has only to release button 23 which brings ratchet bar 57 towards its starting position via the action of spring 54 and along the travel symbolised by arrows F7 and F8 in FIG. 8d. Furthermore, since hook 72a of spring 72 with which cursor 37 is provided, is placed in indexing catch 44 corresponding to zone Z8 of the disposable strip, the latter remains stable in its new position until the cover is closed.

One thus sees that this operating cycle involves an orbital movement of the ratchet bar along an outline which has a closed rectangular curve along the direction of arrows F5 to F8 shown in FIG. 8d.

Of course, this cycle may be repeated for all the measuring zones of disposable strip 34, until only leader zone ZA is left in the apparatus. However, in the corresponding position of cursor 35, this zone is uncoupled from the latter and the user may thus easily remove it from the apparatus so as to be able to introduce a new disposable strip.

In the embodiment which has just been described, the travel on which the disposable strip can be moved by the rotation movement of the cover is determined by the axial length of the helical portion of groove 75. This travel is relatively small due to the fact that a part of the rotation movement of the cover is devoted to the actuation of the cutting edge of cutting unit 32. It is obvious that the travel of the disposable strip over distance w must be accomplished before this cutting edge begins to cut the strip. This is possible due to the fact that the cutting edge is driven by cover 22 with a mechanism of the type connecting rod-crank so that at the beginning of the closing movement of the cover, the rotation travel of the cover is proportionally small in relation to the rectilinear travel of the cutting edge. During this part of the movement, the cutting edge can thus come closer to the strip, while the latter advances in a linear manner over distance w due to the fact that finger 73 follows helical portion 75b of groove 75.

However, it happens that the angle of rotation of the cover does not allow a significant distance w to be obtained, while in certain cases, a distance w which is as significant as possible would be desirable.

This result can be obtained thanks to the alternative embodiments shown in FIGS. 9A to 11.

FIGS. 9A and 9B show a first alternative embodiment of the coupling between cover 22 and guiding plate 58.

As in the embodiment described above, cover 22 comprises a cylindrical extension 74 provided with a groove 75 with a radial portion 75a and a helical portion 75b. This mechanism comprises a hinged lever 76 rotatably mounted on a pivot 77 integral with upper half shell 20A of case 20. This lever 76 comprises a first stud 78 engaged in a notch 80 provided in guiding plate 58. In this case for a longitudinal travel w of guiding plate 58, the axial length a of groove 75 may be smaller in the ratio of the corresponding lengths of lever 76 on either side of its centre of rotation. This lever thus acts as movement amplifier.

An alternative embodiment of this movement amplifier device is shown in FIGS. 10A and 10B. In this case, extension 74 of the axis of cover 22 comprises a flat surface 81. An L-shaped lever 82 is hinged on a pivot 83 which is attached to upper half shell 20A. Its small branch 82a abuts the peripheral surface of extension 75, while its long branch 82b is engaged via its end in notch 80 of guiding plate 58. It is understood that this device also constitutes a movement amplifier, the distance a' corresponding to the amplitude of movement of small branch 82a during the rotation of cover 22, being increased by the ratio of the lengths of the two branches of lever 82, to achieve a displacement w of the guiding plate.

A same effect can be obtained if, according to FIG. 11, small branch 82a of lever 82 is provided with an inverted dihedral surface 84 able to penetrate a complementary shaped groove 85 provided in the peripheral surface of extension 74.

What is claimed is:

1. A dispensing apparatus for use with disposable strips, each comprising several detachable successive utilization zones along its longitudinal axis, said apparatus comprising:

a case with an hinged cover able to move between an open position and a closed position, said case defining a circulation passage having an upstream end for the introduction of said strip and a downstream end at the opposite side, a forward feed mechanism for bringing said strip out of the circulation passage with a constant pitch step by step movement, means for cutting said strip, and a sliding unit, mounted so as to move in said passage, attached to said forward feed mechanism and coupled to the downstream end of a strip when said strip is introduced, wherein said dispenser apparatus also comprises a guiding plate, cooperating with a groove located in a cylindrical extension of said means for cutting said strip, to form means for controlling backward movement of said strip over a predetermined distance less than one forward step after said strip has carried out such a step.

2. A dispenser apparatus according to claim 1, wherein said means for controlling the movement of a strip is coupled to the means for cutting said strip so that said strip is cut only after the backward movement of said strip.

3. A dispenser apparatus according to claim 1, wherein said means for controlling the backward movement of a strip also controls the forward movement of said strip over a distance less than one forward step of said strip.

4. A dispenser apparatus according to claim 1, wherein said means for controlling the movement of a strip is actuated by said cover during the respective opening or closing movement or movements of said cover.

5. A dispenser apparatus according to claim 1, further comprising resilient means carried by said sliding unit for blocking and coupling said sliding unit and said strip, and wherein said sliding unit comprises a cursor mounted so as to slide in said circulation passage and provided with a hooked spring co-operating with said forward feed mechanism.

6. A dispenser apparatus according to claim 5, wherein said forward feed mechanism comprises a ratchet bar co-operating with said hooked spring to assure said coupling and to enable the step by step forward feed of said cursor, and wherein said ratchet bar is coupled to a control button mounted freely in said case to control said step by step movement.

7. A dispenser apparatus according to claim 6, wherein said ratchet bar is mounted in said case parallel to said circulation passage so as to carry out an orbital movement in its own plane, said ratchet bar having serrated edged toothing for, during each orbital movement corresponding to one forward step of said cursor, engaging with said hooked spring.

8. A dispenser apparatus according to claim 7, wherein said orbital movement has a rectangular outline.

9. A dispenser apparatus according to claim 7, wherein said ratchet bar has at least one cut in which a tightening screws, fixed in relation to said case, are engaged to define with said cut said orbital movement.

10. A dispenser apparatus according to claim 7, wherein a resilient return spring is provided for drawing backwards said ratchet bar.

11. A dispensing apparatus according to claim 1, wherein indexing catches are provided in said circulation passage with the pitch of said step by step movement and wherein said hooked spring is arranged to engage with said indexing catches to fix each position of said cursor.

* * * * *